United States Patent [19]

Abrahams et al.

[11] 4,026,803

[45] May 31, 1977

[54] CHROMATOGRAPHIC COLUMN WITH IMPROVED END FITTINGS

[75] Inventors: Louis Abrahams, Worcester; Manuel A. Russo, Framingham, both of Mass.

[73] Assignee: Waters Associates, Milford, Mass.

[22] Filed: Dec. 24, 1975

[21] Appl. No.: 644,179

[52] U.S. Cl. .............................. 210/198 C; 55/386
[51] Int. Cl.² ........................................ B01D 15/08
[58] Field of Search .................. 55/67, 197, 386; 210/198 C, 31 C

[56] References Cited

UNITED STATES PATENTS

| | | | |
|---|---|---|---|
| 3,334,514 | 8/1967 | Catravas | 55/197 |
| 3,440,864 | 4/1969 | Blume | 210/198 C |
| 3,474,908 | 10/1969 | Catravas | 210/198 C |
| 3,682,315 | 8/1972 | Haller | 210/198 C X |
| 3,800,956 | 4/1974 | Nishizawa | 210/198 C |
| 3,855,130 | 12/1974 | Randau et al. | 55/386 X |
| 3,978,575 | 9/1976 | Beyer et al. | 29/427 |

Primary Examiner—John Adee
Attorney, Agent, or Firm—Robert A. Cesari; John F. McKenna; Andrew F. Kehoe

[57] ABSTRACT

Novel end fitting assemblies of particular advantage for use on liquid chromatographic columns, and novel chromatographic columns comprising these novel end fittings. The end-fittings are characterized by (a) very low dead space; (b) economical and convenient replacement of wearing parts; with minimal disturbing of the packed column, or other functional end-fitting components such as cones, filters, etc. A particular advantage is the design whereby the connector portions of the fitting assembly are not normally wetted by process fluids during operation of the column. Thus, the connector portions of the assemblies can be selected from a wide variety of mechanically-desirable materials selected for their wearing characteristics. Moreover, the fittings can be tightened for high-pressure operation without damage to the structure of the column of which they are used.

4 Claims, 2 Drawing Figures

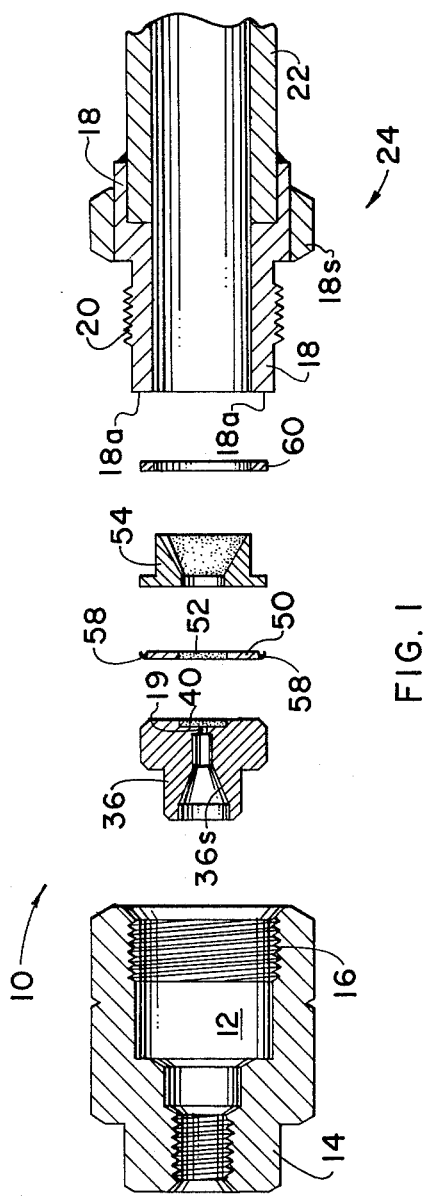
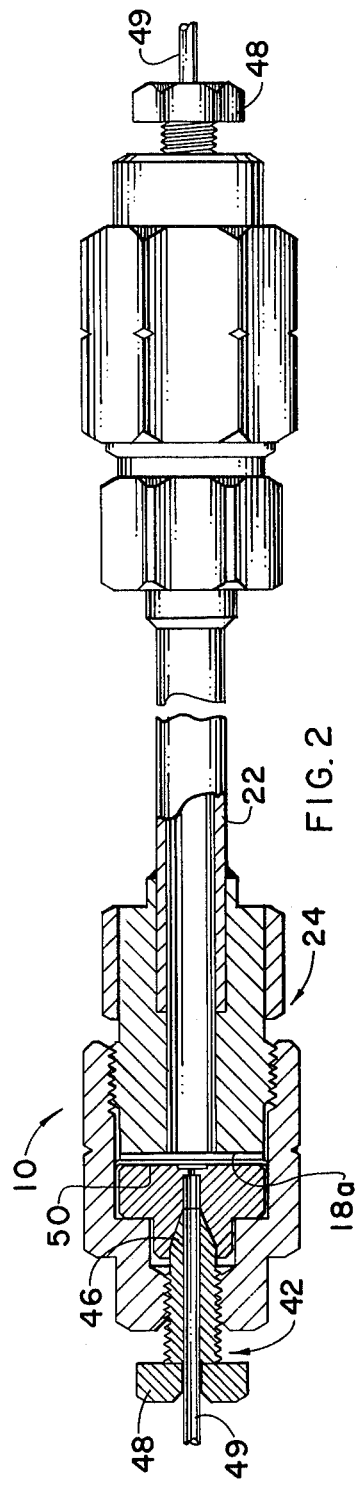

CHROMATOGRAPHIC COLUMN WITH IMPROVED END FITTINGS

BACKGROUND OF THE INVENTION

Liquid chromatography is a process used increasingly in analytical and preparative chemistry, whereby a stationary porous material is held in a chamber, such as a long column, while a mobile liquid material is passed through the porous material. In a typical case, the stationary material is an inert powder coated with a stationary liquid agent. Various distinct chemical compounds contained in a carrier liquid (which usually forms the bulk of the mobile liquid) have varying affinities for the stationary liquid agent. Consequently, as the mobile liquid moves through a chromatographic column, various chemical compounds are, as a consequence of their different affinities delayed varying times by their contact with the stationary liquid agent. These various chemicals emerge from the column at different times and are detected individually by a refractometer, an ultra violet light, absorbtometer or some other such analytical apparatus in which the liquid flows on leaving the chromatographic column.

Over the years a good deal of inventive effort has been devoted to the development of equipment for use in liquid chromatography. Much of this effort has been devoted to the design of equipment which would tend to idealize the distribution and flow of the mobile phase through the porous stationary phase. See, for example, U.S. Pat. Nos. 3,522,172, 3,374,606, 3,250,058, and 3,796,657 all of which relate to flow-distribution means placed within the column. Some of the work has been primarily directed to the design of end fittings to optimize the initial distribution of the mobile liquid at the top of the column. See, for example, U.S. Pat. No. 3,334,514 to Catravas and U.S. Pat. No. 3,511,377 to Hrdina wherein conical entrances are disclosed. Other work has related specifically to avoiding preferential flow of liquid between the walls of a column and the packing therein; e.g. see U.S. Pat. No. 3,808,125 to Good.

Problems associated with the design and use of end fittings are particularly difficult when high pressure chromatography is used. Pressures in the range of 1000–6000 psig are frequently used in liquid chromatography. Consequently, very dependable sealing techniques must be used and it is a problem to assure adequate sealing without excessive wear of deformed metal parts. For example, some fittings have ferrules which are tightened about the columns. After use, the shape of the column is materially distorted by the force exerted on the ferrule during tightening of end fittings.

One of the more successful approaches to closing a high-pressure column is the use of a compression screw and ferrule assembly as sold by Waters Associates, Inc. of Milford, Massachusetts. In such a device, the liquid seal between a liquid inlet pipe and the column is achieved by forcing the inlet pipe downwardly with compression screw to form a metal-to-metal seal with the fitting member. The seal is adequate, but there is a necessity of replacing, from time-to-time, the metal-sealing parts.

Applicants, as a consequence of the various problems associated with the end fittings used on chromatographic columns have undertaken to provide a column with superior fittings as is disclosed hereinbelow.

SUMMARY OF THE INVENTION

It is a principal object of the present invention to provide a column structure for use in liquid chromatography which column comprises end fittings which are operable at pressures of 5000 psig and above, but which are economical to maintain and which can be utilized many times without mechanically damaging the columns.

Another object of the invention is to provide an end fitting assembly the wearing parts of which can be changed without disturbing the column packing.

It is another object of the invention to provide the novel end-fitting assemblies which allow construction of the liquid chromatographic columns described in the objects listed hereinabove.

Another object of the invention is to provide end fittings for a liquid chromatographic column which (1) comprise external non-wetted fitting members which can be selected for their mechanical properties rather than for chemically inert characteristics, and which (2) comprise internal parts which can be easily and inexpensively replaced, and which bear the brunt of the mechanical forces required to seal the column.

A further object of the invention is to achieve the above object while simultaneously achieving little or no dead volume in the fittings.

Other objects of the invention will be obvious to those skilled in the art on their reading of this disclosure.

The above objects have been largely achieved by the rise of end-fitting assemblies which will be described in detail below. These assemblies have at least some, and preferably all, of the following characteristics.

1. No substantial liquid or "void" volume. Excess liquid volume or flow path can result in the undesirable phenomena known as peak-spreading, i.e. a sample entering the chromatographic packing over an extended time because the sample has been spread out in the apparatus between the injection point and the packing.
2. Wearing parts can be readily replaced without disturbing the column packing.
3. Flow-influencing parts (including filter means) can be readily removed, or changed to alter characteristics, without disturbing the column packing.
4. Housing means whereby the various flow influencing parts (including filter means) of the fittings are held in position are not wetted with process liquids, consequently can be selected from a wide variety of materials of construction to optimize their long-term wearing characteristics. Thus, such housing or positioning means can be made integral with the column itself because they wear well over the entire life of the column.

ILLUSTRATIVE EXAMPLE OF THE INVENTION

In this application and accompanying drawings, there is shown and described a preferred embodiment of the invention and suggests various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

FIG. 1 is an exploded view, in section of end fitting according to the instant invention.

FIG. 2 is an assembled chromatographic column partly in section.

Referring to FIG. 1, it has seen that end-fitting assembly 10 comprises a housing chamber 12 formed of a terminal fitting member 14. Fitting member 14 comprises an internal screw thread 16 which is adapted for attachment to external screw thread 20 of fitting member 18. Fitting member 18 is permanently connected, as by brazing, welding, or any other suitable manipulative process known to the art, to a tubing 22 of Type 316 stainless steel, which forms the primary conduit member of liquid chromatographic column structure 24, and to stainless steel sleeve 18s. The upper edge 18a of fitting 18 forms means to support certain removable members to be described below. Sleeve 18s is formed out of heat-treated Type 410 stainless steel and provides a hardened, wear resistant, tool-engaging surface.

Fitting members 14 and 18 are advantageously formed of dissimilar materials. Members 14, the terminal fitting most convenient to manipulate and normally subjected to the greatest stress, being formed of a heat-hardenable material, e.g. Type 410 stainless steel. Fitting can be formed of a heat-hardenable material, e.g. Type 410 stainless steel. Fitting 18 can be formed of a softer, but a more chemically inert material such as Type 316 stainless steel. However, the fact that fitting member 18 is not wetted by process fluids allows other materials to be selected if this is desired.

In general, tubing 22 is advantageously formed of Series 300 stainless steels. However, it is recommended that Type 303 stainless be avoided for general purpose use.

When liquid is being pumped into the column, it enters through a compression screw-and-ferrule assembly 42 as seen in FIG. 2. The ferrule 46 is screwed down with the compression screw 48 to form a seal with fitting structure. Most of the force is carried by hardened threads 16 of fitting member 14 and the ferrule-sealing bearing surface 36s of filter insert member 36. Although assembly 36 is formed of 316 stainless steel, and somewhat susceptible to wear and deformation over periods of extended use, it is easily and economically replaced without disturbing the packed chromatographic column.

Process liquid flowing through inlet tube 49 of assembly 42 proceeds through a filter insert assembly 36 comprising, typically, a microfilter 40 which, advantageously, has a nominal 2-micron particle-size retention rating. "Microfilter" as used herein is indicative of a nominal aperture sized in the micron range.

After the liquid passes through the filter, it moves through a thin retainer plate 50 the central passage 52 of which is advantageously formed of a fine mesh material. The primary function of plate 50 mesh is to serve as a means to maintain the filter 40 in place. It is formed of a work-hardened stainless steel (Type 316) and also acts as an anti-galling buffer member. Use of small flexible projections 58 about the periphery of plate 50 help retain plate 50 against substantial axial movement within chamber 12. Also, the apertured central passage 52 comprises a sufficient volume of solid material therein (about 10,000 etched holes per inch) to make a substantial reduction in the liquid volume within the assembly 10.

On leaving retainer plate 50, the liquid goes through cone distributor member 54. The space within this annularly-shaped member 54 is filled with porous, solid material. Advantageously, the space is filled by a chromatographic packing material, but it may be filled with a fritted material, with glass beads, or with any other such porous material. The removable nature of cone member 54 facilitates changing the angle of the cone as is advantageous for different conditions of flow, e.g. different flow rates, use of different packing materials, or the like.

Washer 60 forms means to aid sealing collar 60 of the cone distributor 54 against surface 18a of fitting 18. The washer is advantageously formed of Type 316 stainless steel and is optional in structures of the type illustrated.

There is essentially no deadspace for liquid hang-up in the illustrated fittings. Moreover, there is little or no excess liquid volume at all between the inlet at the bottom of conduit 19 in member 36 to the start of the porous solid material, advantageously chromatographic packing comprising an immobile distributor member 54.

Use of the above-described end fitting is often desirable at both the top and bottom of liquid chromatography columns; although, in many columns, it is advantageously utilized at the inlet end of the column only.

It is to be understood that the following claims are intended to cover all of the generic and specific features of the invention herein described and all statements of the scope of the invention which might be said to fall therebetween.

What is claimed is:

1. In a packed column adapted for use in liquid chromatography, said column comprising a tubular section, and end-fitting assemblies at the inlet and outlet of said tubular section and said end fittings at the inlet of said column comprise:
   a. a first threaded connector member said first connector is permanently attached to an end of said tubing,
   b. a second, complementary, threaded fitting member, adapted for attachment to said tubing and forming, with said first connector member, a chamber in which to house parts wetted by any said process liquid passing through said column,
   c. said process-wetted parts forming a conduit between the end of said column and the adjacent end of said column, the improvement wherein said conduit comprises substantially no liquid dead space and said process-wetted parts are supported on said permanently attached connector and comprise, at least,
   1. a filter insert assembly, adapted for compression between said connector members and comprising, at the end of said filter insert assembly which is most remote from said tube, a bearing surface adapted to receive and form a metal-to-metal seal with a liquid feed tube and, at the end of said insert assembly nearest said tube, a micro-filter
   2. and a retainer plate comprising a central passage formed of a large number of minute holes and also having means to engage the internal wall of a said exterior connector member;

d. and wherein said filter insert assembly is readily removable from said housing without disturbing said packed column.

2. A column as defined in claim 1 comprising a cone distributor member mounted as the large end of said cone is adjacent to the end of said tubular section.

3. A column as defined in claim 1 wherein said tubular section is formed of a 300 series stainless steel, but wherein exterior bearing surfaces of said connector members are formed of a relatively hard stainless steel.

4. A column as defined in claim 2 wherein said filter insert assembly is separated from said cone distributor member by a retainer plate which is restricted from easy movement parallel to the axis of said tubular section.

* * * * *